(12) United States Patent
Chen et al.

(10) Patent No.: US 11,710,802 B2
(45) Date of Patent: Jul. 25, 2023

(54) SENSING DEVICE

(71) Applicants: LITE-ON OPTO TECHNOLOGY (CHANGZHOU) CO., LTD., Changzhou (CN); LITE-ON TECHNOLOGY CORPORATION, Taipei (TW)

(72) Inventors: Hung-Jui Chen, New Taipei (TW); Po-Jui Lin, New Taipei (TW)

(73) Assignees: LITE-ON OPTO TECHNOLOGY (CHANGZHOU) CO., LTD., Changzhou (CN); LITE-ON TECHNOLOGY CORPORATION, Taipei (TW)

( * ) Notice: Subject to any disclaimer, the term of this patent is extended or adjusted under 35 U.S.C. 154(b) by 218 days.

(21) Appl. No.: 16/991,697

(22) Filed: Aug. 12, 2020

(65) Prior Publication Data

US 2021/0050471 A1 Feb. 18, 2021

Related U.S. Application Data

(60) Provisional application No. 62/885,872, filed on Aug. 13, 2019.

(30) Foreign Application Priority Data

Jul. 20, 2020 (CN) .......................... 202010701758.3

(51) Int. Cl.
*H01L 31/12* (2006.01)
*H01L 33/62* (2010.01)
(Continued)

(52) U.S. Cl.
CPC ............ *H01L 31/12* (2013.01); *H01L 25/167* (2013.01); *H01L 31/0203* (2013.01);
(Continued)

(58) Field of Classification Search
CPC ............... H01L 31/12; H01L 31/02005; H01L 31/0203; H01L 31/02164; H01L 33/52;
(Continued)

(56) References Cited

U.S. PATENT DOCUMENTS 9,362,205 B2 6/2016 Shibasaki et al.
2003/0183928 A1 10/2003 Miyazawa
(Continued)

FOREIGN PATENT DOCUMENTS

CN 102809764 A 12/2012
CN 103262238 A 8/2013
(Continued)

*Primary Examiner* — Tu-Tu V Ho
(74) *Attorney, Agent, or Firm* — Li & Cai Intellectual Property (USA) Office

(57) ABSTRACT

A sensing device includes a substrate, two chips, and a shielding structure. The two chips are respectively defined as an emitting chip and a receiving chip. The emitting chip can emit a sensing light beam, the receiving chip can receive the sensing light beam, and the two chips are fixed in position on the substrate at intervals. At least one of the chips is electrically connected to the substrate through at least one wire, and a position where the wire is connected to the substrate is located between the two chips. The shielding structure is formed on the substrate. The shielding structure is located between the two chips, and the shielding structure covers the wire and a portion of the chip connected to the wire. Compared with the conventional photo-plethysmography sensor, the sensing device has the advantage of a smaller size.

3 Claims, 22 Drawing Sheets

(51) Int. Cl.
  *H01L 31/02*    (2006.01)
  *H01L 31/0216*  (2014.01)
  *H01L 31/0203*  (2014.01)
  *H01L 33/52*    (2010.01)
  *H01L 25/16*    (2023.01)
  *H01L 31/173*   (2006.01)
  *A61B 5/024*    (2006.01)

(52) U.S. Cl.
  CPC .. *H01L 31/02005* (2013.01); *H01L 31/02164* (2013.01); *H01L 31/173* (2013.01); *H01L 33/52* (2013.01); *H01L 33/62* (2013.01); *A61B 5/02427* (2013.01); *A61B 2562/0233* (2013.01); *A61B 2562/185* (2013.01)

(58) Field of Classification Search
  CPC ....... H01L 33/62; H01L 25/167; H01L 33/56; H01L 31/173; A61B 5/02427; A61B 2562/0233; A61B 2562/185; A61B 5/14552
  USPC .......................................................... 257/82
  See application file for complete search history.

(56) References Cited

U.S. PATENT DOCUMENTS

| | | |
|---|---|---|
| 2003/0215982 A1 | 11/2003 | Shimizu |
| 2003/0234434 A1 | 12/2003 | Matsushima |
| 2010/0213563 A1 | 8/2010 | Lai |
| 2016/0061653 A1* | 3/2016 | Chang ................... H01L 25/167 250/237 R |

FOREIGN PATENT DOCUMENTS

| | | |
|---|---|---|
| CN | 103383457 A | 11/2013 |
| CN | 104332524 A | 2/2015 |
| CN | 205752171 U | 11/2016 |
| CN | 108269793 A | 7/2018 |
| JP | 2015216228 A | 12/2015 |
| TW | M257518 U | 2/2005 |
| TW | 201723528 A | 7/2017 |
| TW | 201824524 A | 7/2018 |

* cited by examiner

SENSING DEVICE

CROSS-REFERENCE TO RELATED PATENT APPLICATION

This application claims the benefit of priority to China Patent Application No. 202010701758.3, filed on Jul. 20, 2020 in People's Republic of China. The entire content of the above identified application is incorporated herein by reference.

This application claims priority from the U.S. Provisional Patent Application Ser. No. 62/885,872 filed Aug. 13, 2019, which application is incorporated herein by reference in its entirety.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a sensing device, and more particularly to a sensing device suitable for wearable devices.

BACKGROUND OF THE DISCLOSURE

A conventional wearable device uses a photo-plethysmography sensor (PPG sensor) to measure a heart rate or blood oxygen of a user. However, the conventional photo-plethysmography sensor is difficult to be reduced in size based on current manufacturing methods, which limits the range of application of the photo-plethysmography sensor.

SUMMARY OF THE DISCLOSURE

In response to the above-referenced technical inadequacies, the present disclosure provides a sensing device, which is mainly used to improve the problem that a size of a conventional photo-plethysmography sensor used in a wearable device is difficult to be reduced.

In one aspect, the present disclosure provides a sensing device which includes a substrate, two chips, and a shielding structure. The two chips are respectively defined as an emitting chip and a receiving chip. The emitting chip is capable of emitting a sensing light beam, the receiving chip is capable of receiving the sensing light beam, and the two chips are fixed in position on the substrate at intervals. At least one of the chips is electrically connected to the substrate through at least one wire, and a position where the wire is connected to the substrate is located between the two chips. The shielding structure is formed on the substrate. The shielding structure is located between the two chips, and the shielding structure covers the wire and a portion of the chip connected to the wire.

Preferably, each of the chips is electrically connected to the substrate through at least one wire, each of the wires is covered by the shielding structure, and the shielding structure covers the portion where each of the chips is connected to the at least one wire.

Preferably, in a top view of the sensing device, a sum of a distance from a position where each of the wires is connected to the substrate to a position where each of the wires is connected to the chip is smaller than a width of the shielding structure.

Preferably, a height of the shielding structure is greater than a height of each of the chips.

Preferably, the sensing device further includes: an encapsulant, and the encapsulant covers each of the chips.

Preferably, the encapsulant is configured to absorb light outside a wavelength band corresponding to the sensing light beam.

Preferably, a sum of a height of each of the chips and a thickness of the encapsulant is not greater than a height of the shielding structure.

Preferably, the substrate has a mounting surface, and the two chips and the shielding structure are disposed on the mounting surface. The sensing device further includes a blocking structure disposed on the mounting surface, and the blocking structure is disposed around the two chips and the shielding structure.

Preferably, a height of the blocking structure is not less than a height of each of the chips.

Preferably, the sensing device further includes at least an encapsulant, and the encapsulant covers each of the chips and the blocking structure.

Preferably, the sensing device further includes at least a ring-shaped blocking structure, the ring-shaped blocking structure is formed on the blocking structure, and the ring-shaped blocking structure is disposed around the two chips and the shielding structure.

Preferably, the ring-shaped blocking structure, the shielding structure, and the two chips jointly form at least one accommodating groove. The sensing device further includes an encapsulant, and the encapsulant is disposed in the accommodating groove.

Preferably, a top surface of the ring-shaped blocking structure, a top surface of the shielding structure, and a top surface of the encapsulant are flush with each other.

Therefore, the sensing device of the present disclosure can be effectively reduced in size by virtue of "the shielding structure being disposed between the emitting chip and the receiving chip", and by virtue of "the shielding structure covering the wire and a portion of the chip connected to the wire".

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

Figure 1:
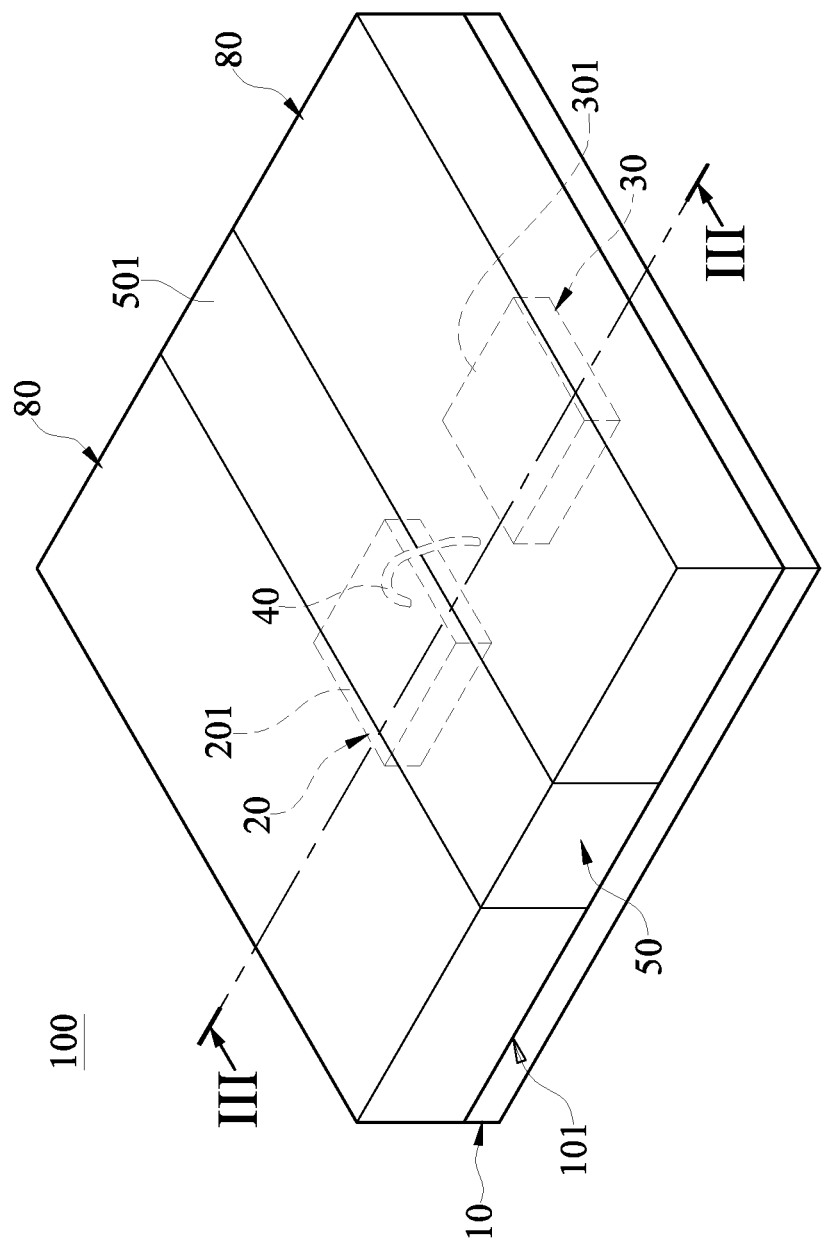
FIG. 1 is a perspective view of a sensing device according to a first embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Figure 2:
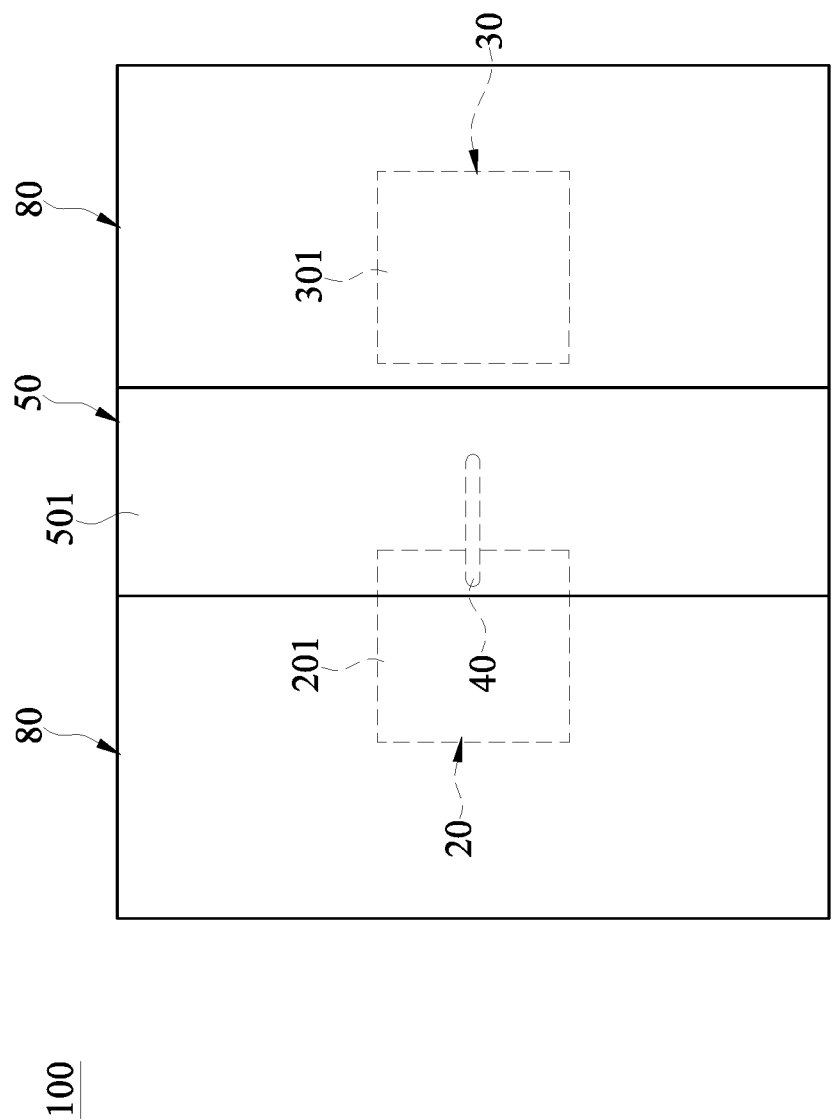
FIG. 2 is a top view of the sensing device according to the first embodiment of the present disclosure.
Figure 3:
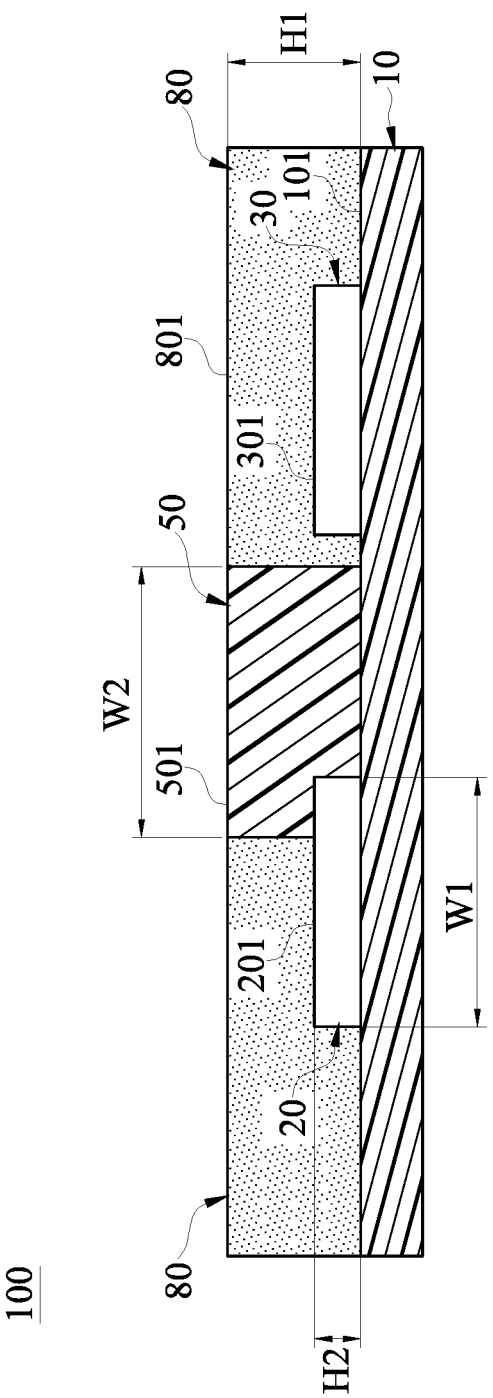
FIG. 3 is a cross-sectional view of the sensing device according to the first embodiment of the present disclosure.

Referring to FIG. 1 to FIG. 3, FIG. 1 is a perspective view of a sensing device according to a first embodiment of the present disclosure, FIG. 2 is a top view of the sensing device according to the first embodiment of the present disclosure, and FIG. 3 is a cross-sectional view of the sensing device according to the first embodiment of the present disclosure. The sensing device 100 of the present disclosure includes: a substrate 10, two chips (respectively defined as an emitting chip 20 and a receiving chip 30), a wire 40, a shielding structure 50, and an encapsulant 80. The two chips are fixedly disposed on the substrate 10. The two chips are electrically connected to an external power supply unit through the substrate 10. The external power supply unit is configured to provide the power required for an operation of the two chips through the substrate 10. The substrate 10 may be various types of circuit boards according to requirements, and the present disclosure is not limited thereto.

The emitting chip 20 is configured to emit a sensing light beam, and the receiving chip 30 is configured to receive the sensing light beam. The two chips are fixed in position on the substrate 10 and spaced apart from each other. One of the two chips is electrically connected to the substrate 10 through the wire 40. The position where the wire 40 is connected to the substrate 10 is located between the two chips. Another one of the two chips can be fixed on the substrate 10 in a non-wired manner. For example, the another one of the two chips may be a flip-chip. In the present embodiment, the emitting chip 20 is electrically connected to the substrate 10 through the wire 40, but the present disclosure is not limited thereto. In different embodiments, the receiving chip 30 may be electrically connected to the substrate 10 through the wire 40.

In practical applications, the emitting chip 20 is configured to emit green light (sensing light beam), and a relevant processor is configured to calculate a heart rhythm signal of a user according to the green light received by the receiving chip 30, or the emitting chip 20 is configured to emit red light or far-infrared light, and the relevant processor is configured to calculate a blood oxygen concentration of the user based on the red light or far-infrared light received by the receiving chip 30.

The shielding structure 50 is formed on the substrate 10, and the shielding structure 50 is located between the two chips. The shielding structure 50 covers the wire 40 located between the two chips, and the shielding structure 50 also covers a portion of the chip connected to the wire 40. That is, the wire 40 is entirely covered by the shielding structure 50, and the portion of the chip connected to the wire 40 is also covered by the shielding structure 50. The shielding structure 50 is mainly used to shield the sensing light beam, and to prevent the sensing light beam emitted by the emitting chip 20 from directly entering the receiving chip 30, thereby avoiding interference with the receiving chip 30, and also protecting the wire 40. In practical applications, a material of the shielding structure 50 may be determined according to a wavelength of the sensing light beam, and the present disclosure is not limited thereto. The shielding structure 50 may be made of a white material or a black material, or the shielding structure 50 may be made of a material with the same color as the light beam emitted by the emitting chip 20.

In practical applications, a height H1 of the shielding structure 50 is greater than a height of each of the chips. As shown in FIG. 3, in a preferred application, the height H1 of the shielding structure 50 is greater than a sum of a height H2 of the emitting chip 20 and a width W1 of the emitting chip 20, divided by 2*tan θ. θ is a half-value angle of the emitting chip 20. The above proportional relationship can be expressed mathematically as: H1=(H2+W1)/(2*tan θ). For example, assuming that the height of the emitting chip 20 is 150 micrometers (um), the viewing angle of the emitting chip 20 is 120°, and the width of the emitting chip 20 is 280 micrometers (um), the height of the shielding structure 50 may be: (150+280)/(2*tan 60°)=124.13 micrometers (um). In addition, in a preferred application, a difference between the height H1 of the shielding structure 50 and the height of each of the chips is not greater than 50 micrometers (um), and the width W2 of the shielding structure 50 is between 0.5 millimeter (mm) and 0.85 millimeter (mm).

It is worth mentioning that, in the drawings of the present embodiment, the shielding structure 50 only covers the wire 40 located between the two chips and a portion of one of the chips connected to the wire 40, and the shielding structure 50 does not cover the other chip as an example for illustration, but the present disclosure is not limited thereto.

The encapsulant 80 is disposed on the substrate 10, and the encapsulant covers the portions of the two chips not covered by the shielding structure 50. The encapsulant 80 is mainly used to protect the two chips, and the encapsulant 8 provides the light beam emitted by the emitting chip 20 to pass there through. In practical applications, a top surface 801 of the encapsulant 80 may be flush with a top surface 501 of the shielding structure 50, but the present disclosure is not limited thereto.

As described above, a size of the sensing device 100 of the present embodiment can be effectively reduced by virtue of "the shielding structure 50 being located between the emitting chip 20 and the receiving chip 30", and by virtue of "the shielding structure 50 covering the wire 40 and a portion of the chip connected to the wire 40". For example, in actual testing, in the case of using the same size emitting chip 20 and receiving chip 30, a maximum width of the sensing device 100 of the present embodiment is reduced by 35% compared to a conventional sensing device.

Figure 4:
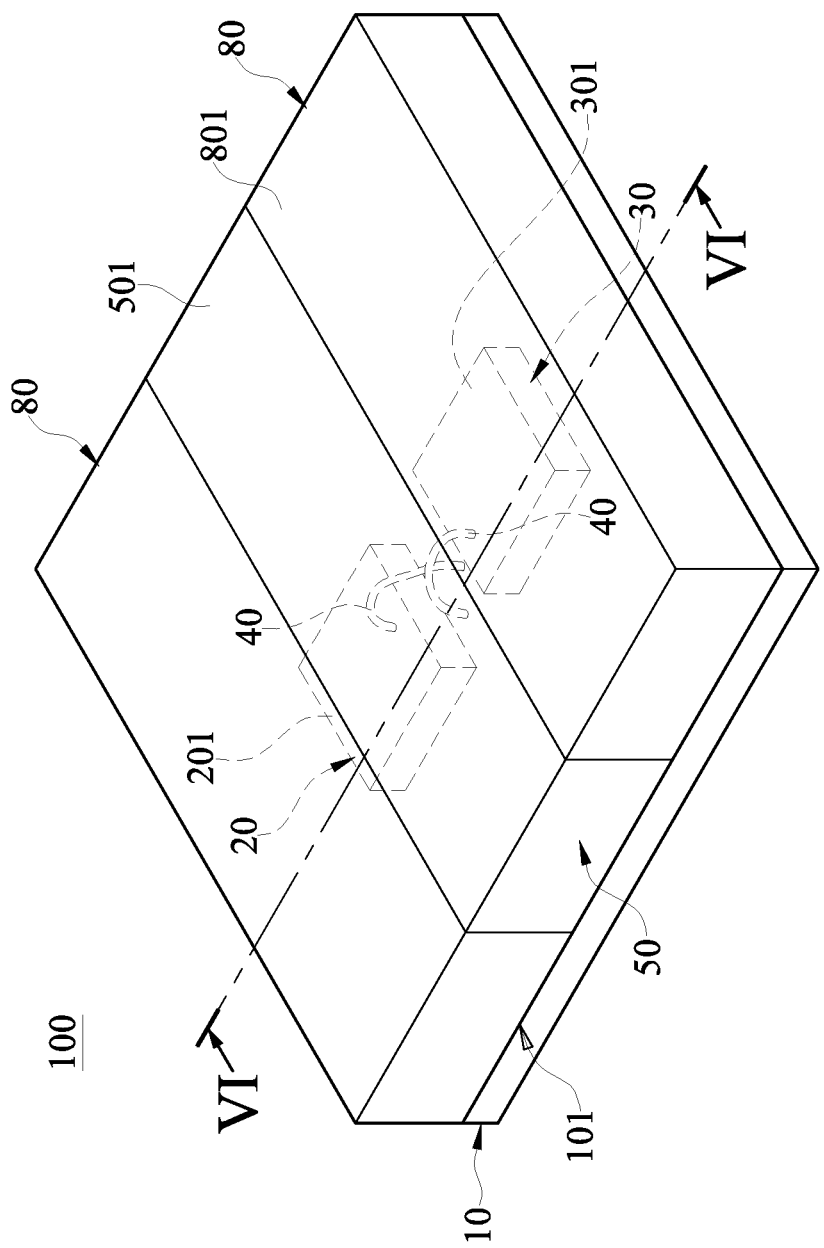
FIG. 4 is a perspective view of a sensing device according to a second embodiment of the present disclosure.
Figure 5:
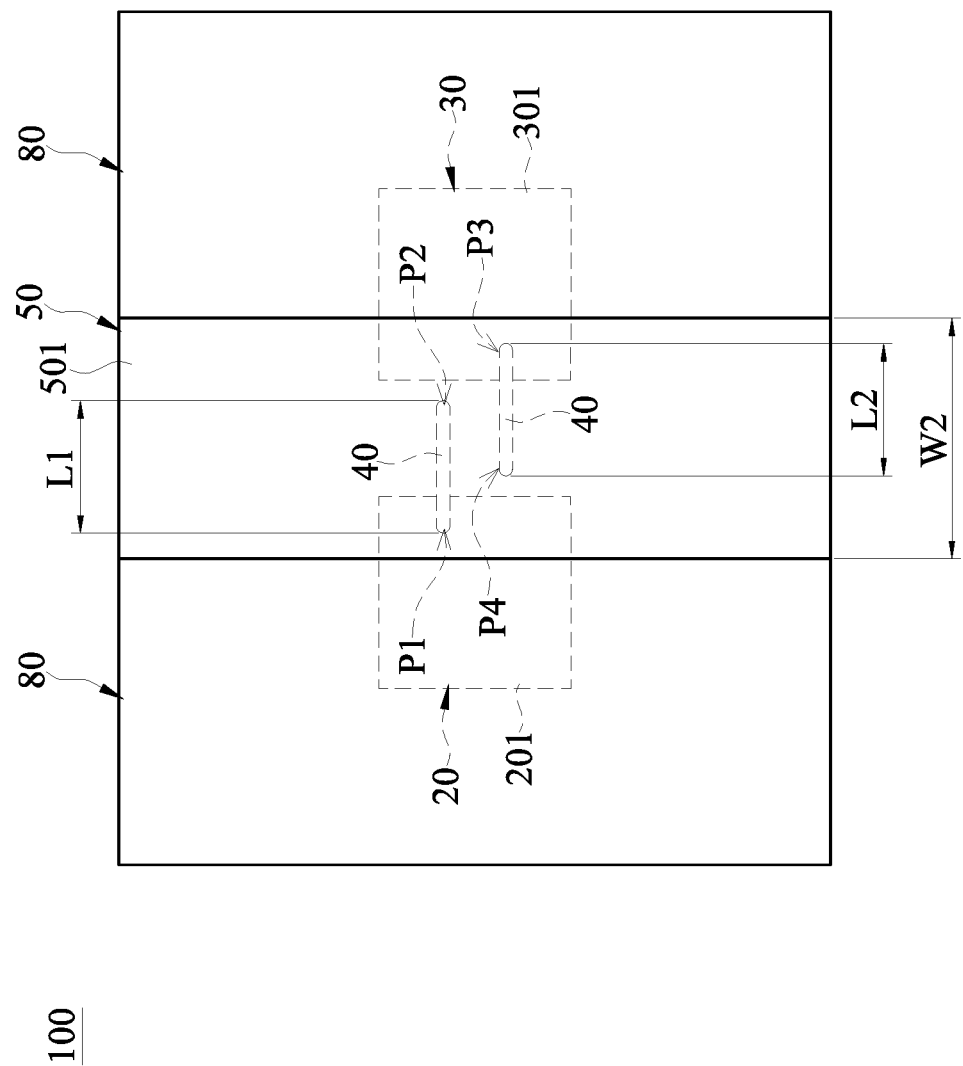
FIG. 5 is a top view of the sensing device according to the second embodiment of the present disclosure.
Figure 6:
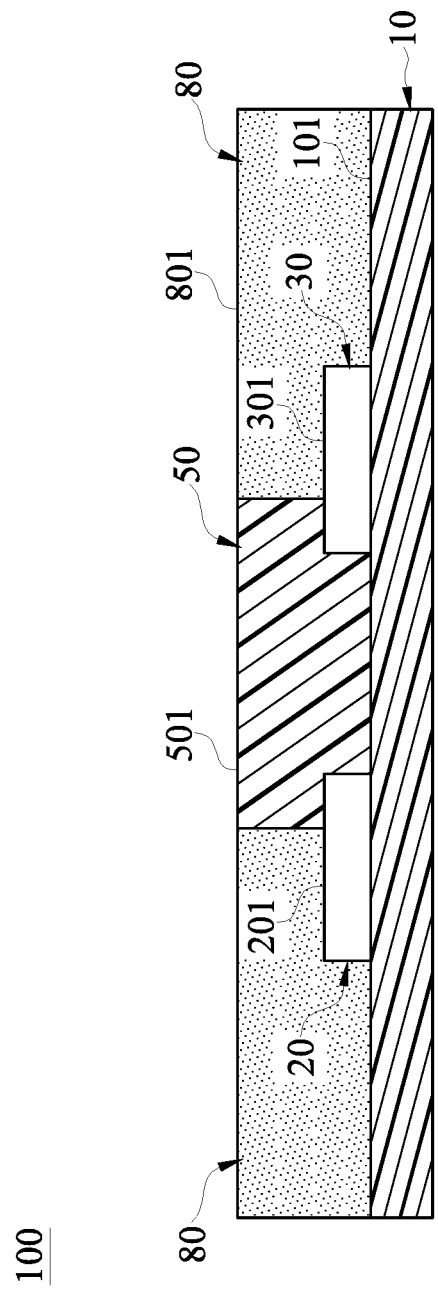
FIG. 6 is a cross-sectional view of the sensing device according to the second embodiment of the present disclosure.

Referring to FIG. 4 to FIG. 6, FIG. 4 is a perspective view of a sensing device according to a second embodiment of the present disclosure, FIG. 5 is a top view of the sensing device according to the second embodiment of the present disclosure, and FIG. 6 is a cross-sectional view of the sensing device according to the second embodiment of the present disclosure. The main difference between the present embodiment and the afore-mentioned first embodiment is that each of the chips (the emitting chip 20 and the receiving chip 30) of the sensing device 100 is electrically connected to the substrate 10 through a wire 40. Each of the wires 40 is covered by the shielding structure 50, and a portion of each of the chips connected to the corresponding wire 40 is also covered by the shielding structure 50.

As shown in FIG. 5, in the top view of the sensing device 100, a sum of a distance from a position where each wire 40 is connected to the substrate 10 to a position where each wire 40 is connected to the chip is greater than a width of the shielding structure 50. More specifically, if a distance from a position P1 where one wire 40 is connected to the emitting chip 20 to a position P2 where the one wire 40 is connected to the substrate 10 is L1, a distance from a position P3 where another wire 40 is connected to the receiving chip 30 to a position P4 where the another wire 40 is connected to the substrate 10 is L2, and the width of the shielding structure 50 is W2, L1+L2≥W2. In other words, as shown in FIG. 6, in the side view of the sensing device 100, the two wires 40 respectively connected to the emitting chip 20 and the receiving chip 30 are arranged alternately.

Figure 7:
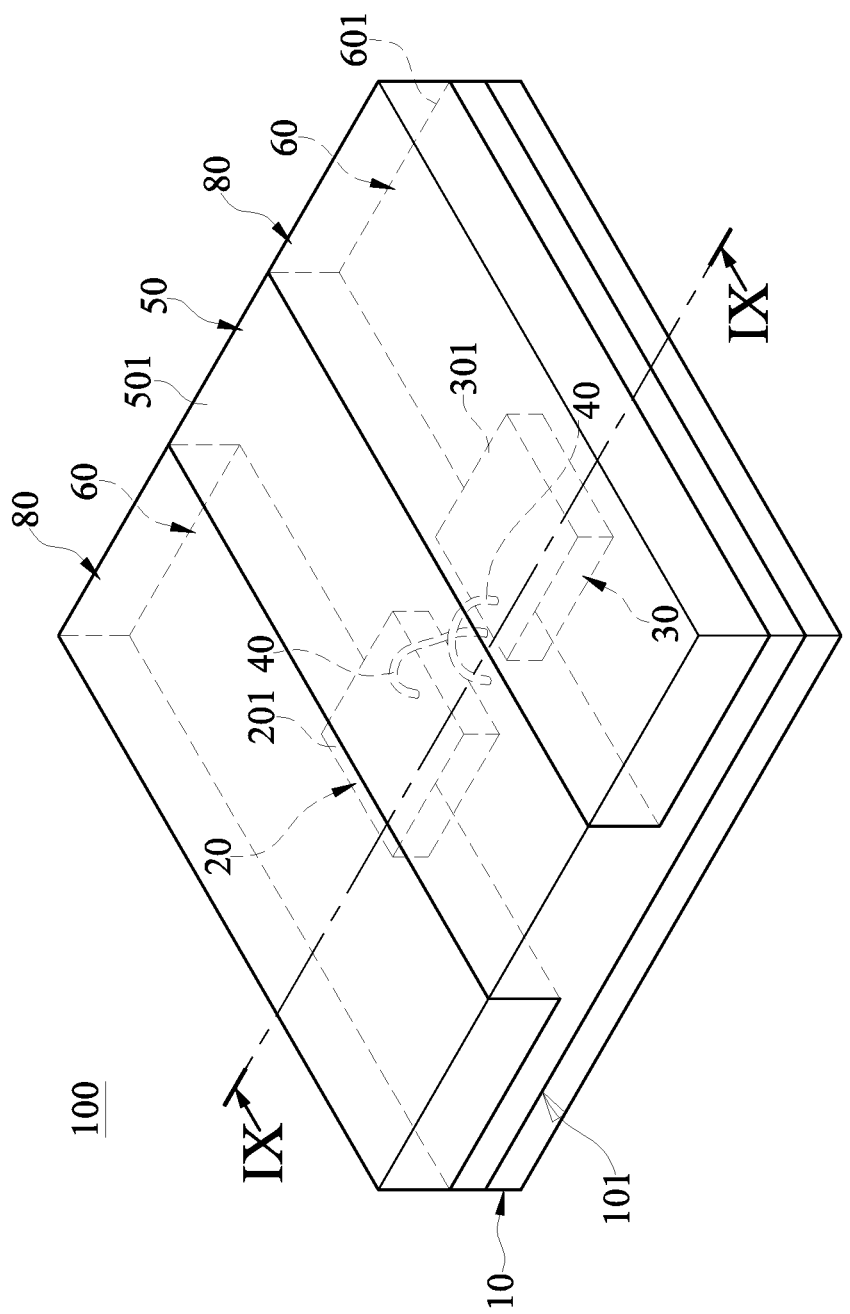
FIG. 7 is a perspective view of a sensing device according to a third embodiment of the present disclosure.
Figure 8:
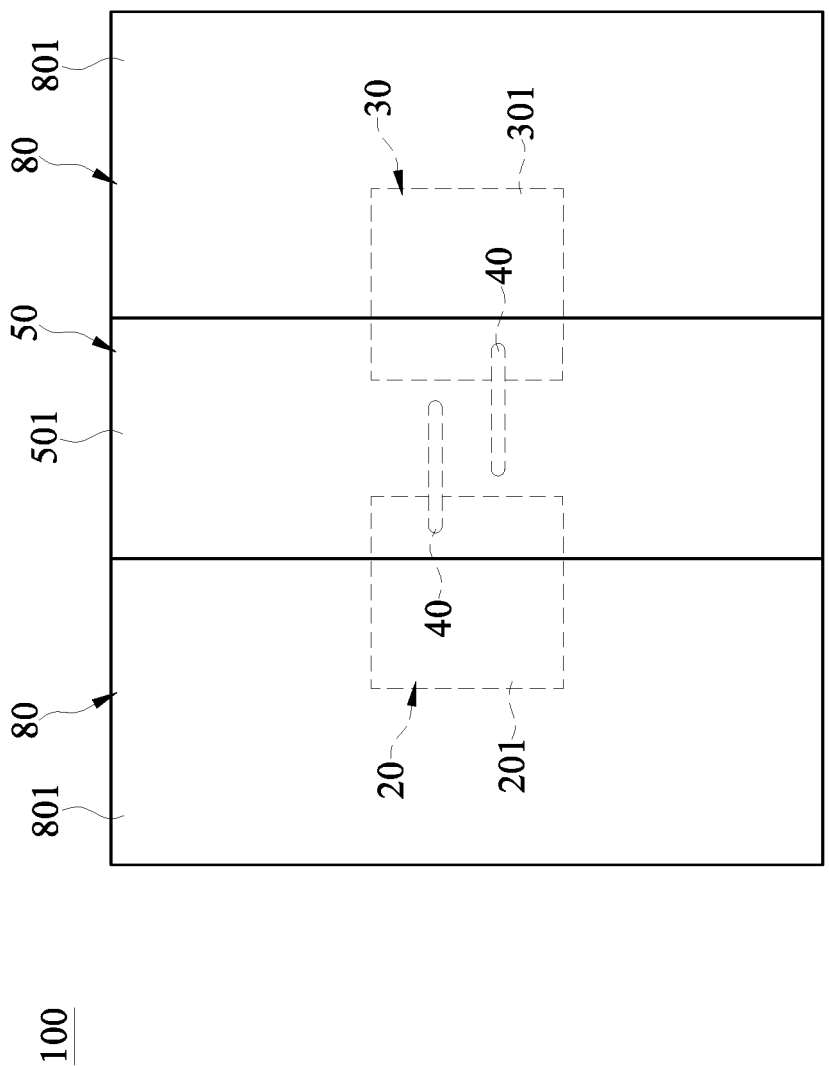
FIG. 8 is a top view of the sensing device according to the third embodiment of the present disclosure.
Figure 9:
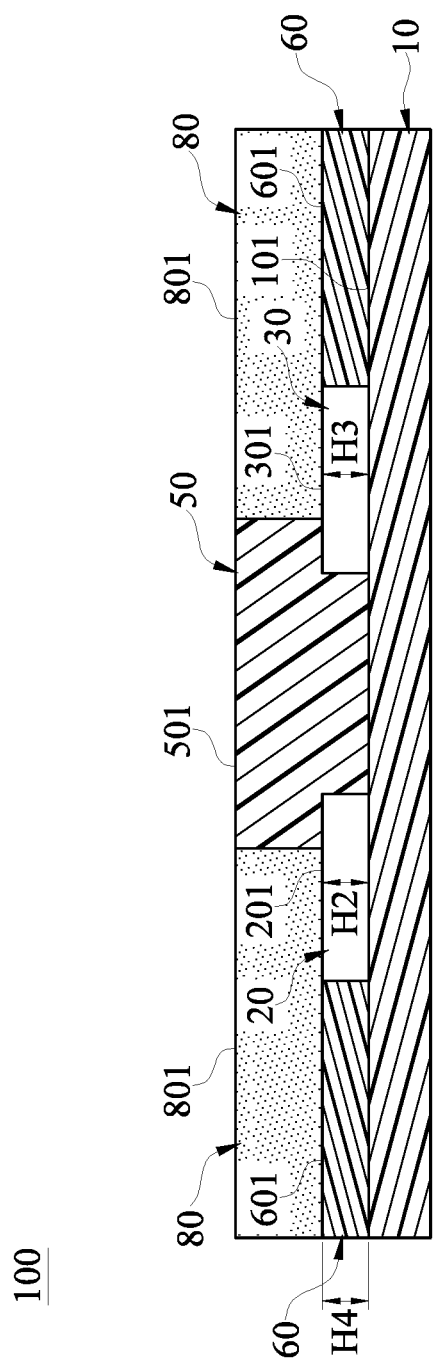
FIG. 9 is a cross-sectional view of the sensing device according to the third embodiment of the present disclosure.

Referring to FIG. 7 to FIG. 9, FIG. 7 is a perspective view of a sensing device according to a third embodiment of the present disclosure, FIG. 8 is a top view of the sensing device according to the third embodiment of the present disclosure, and FIG. 9 is a cross-sectional view of the sensing device according to the third embodiment of the present disclosure. The main difference between the present embodiment and the afore-mentioned second embodiment is that the sensing device 100 may further include a blocking structure 60. The substrate 10 has a mounting surface 101. The emitting chip 20, the receiving chip 30, the shielding structure 50, and the blocking structure 60 are all disposed on the mounting surface 101. The blocking structure 60 is disposed around the emitting chip 20 and the receiving chip 30. That is, except for an emitting surface 201 of the emitting chip 20 away from the substrate 10, the other side surfaces of the emitting chip 20 are covered by the blocking structure 60. In addition, except for a receiving surface 301 of the receiving chip 30 away from the substrate 10, the other side surfaces of the receiving chip 30 are covered by the blocking structure 60.

The blocking structure 60 can be used to prevent a sensing light beam emitted by the emitting chip 20 from directly entering a side surface of the receiving chip 30, and the blocking structure 60 may also be used to absorb the light outside a wavelength band corresponding to the sensing light beam. In practical applications, the blocking structure 60 and the shielding structure 50 may be made of the same material. The shielding structure 50 and the blocking structure 60 may be integrally formed on the substrate 10, but the present disclosure is not limited thereto. In addition, a height H4 of the blocking structure 60 is not less than the heights H2 and H3 of the chips (the emitting chip 20 and the receiving chip 30). Preferably, a top surface 601 of the blocking structure 60 away from the substrate 10 can be flush with the emitting surface 201 of the emitting chip 20 and the receiving surface 301 of the receiving chip 30. The height H4 of the blocking structure 60 may be between 0.2 millimeters (mm) and 0.3 millimeters (mm). In practical applications, the height H4 of the blocking structure 60 may be correspondingly changed according to the height of each chip, and the present disclosure is not limited to the aforementioned range.

Figure 10:
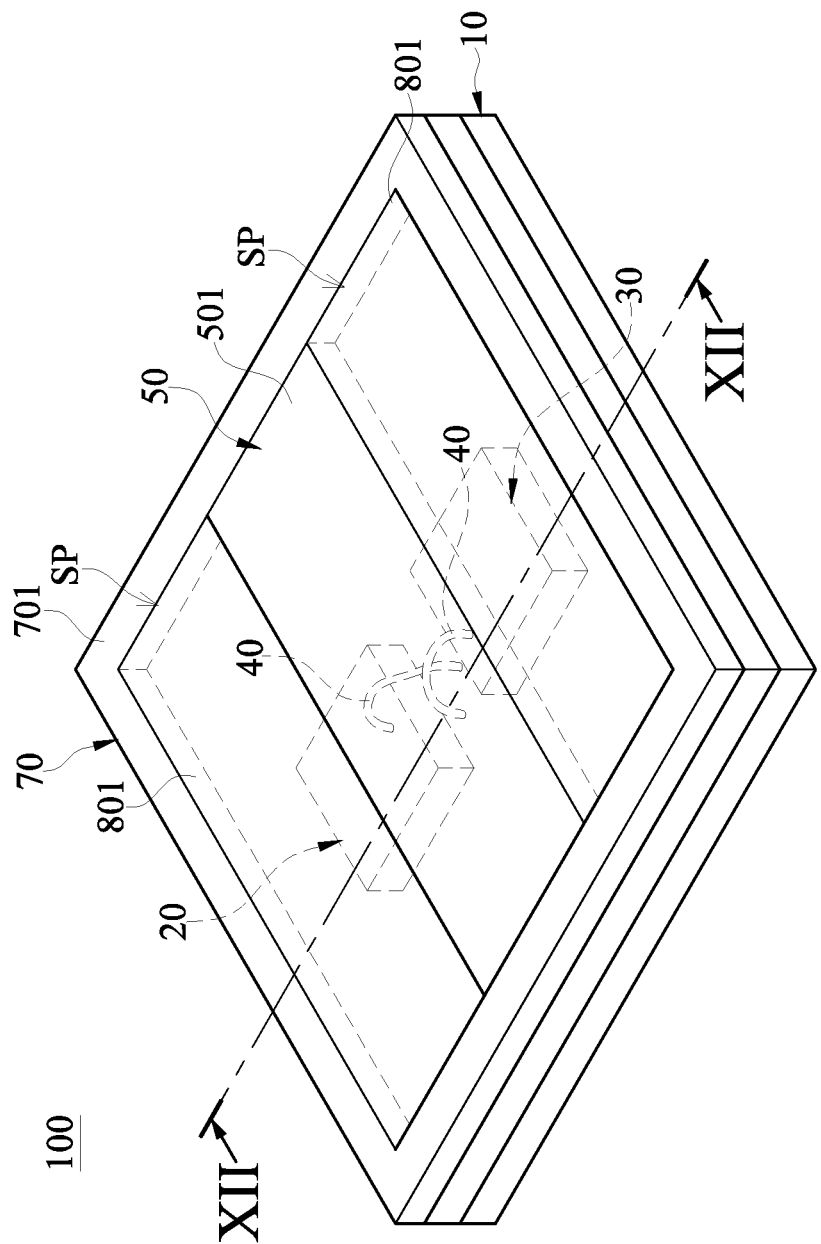
FIG. 10 is a perspective view of a sensing device according to a fourth embodiment of the present disclosure.
Figure 11:
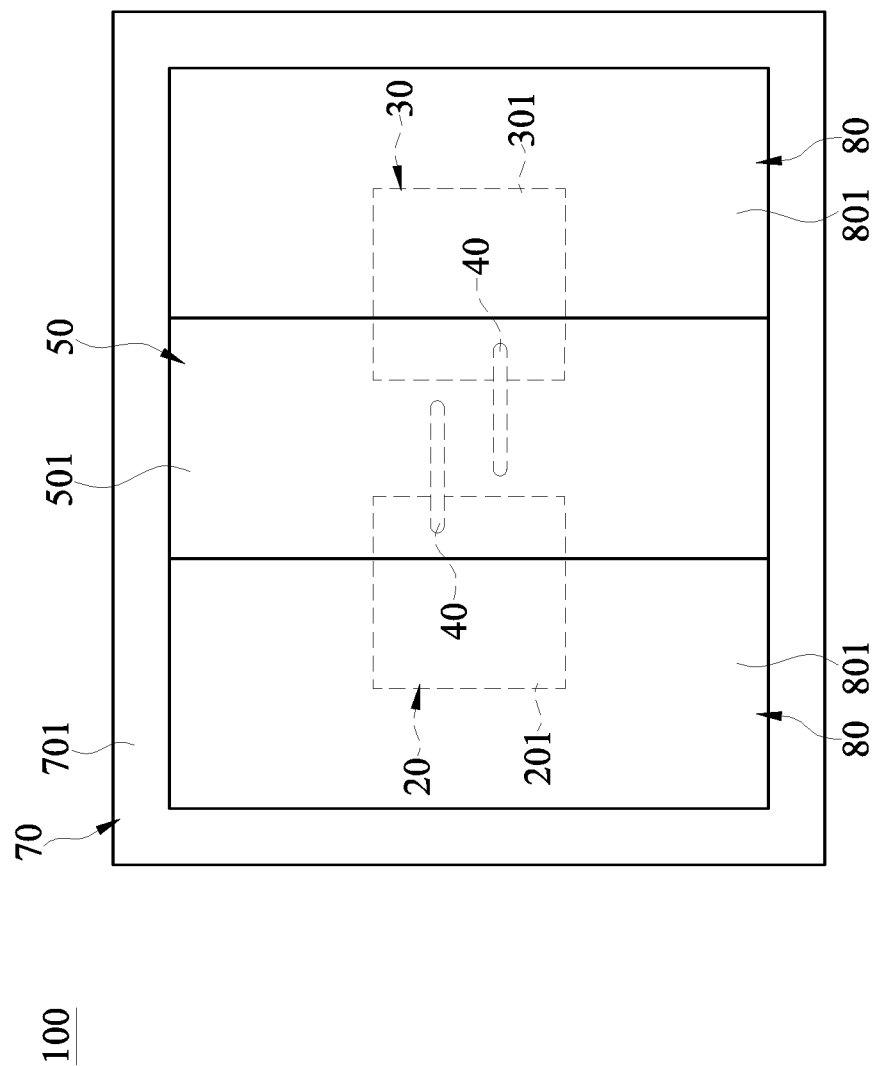
FIG. 11 is a top view of the sensing device according to the fourth embodiment of the present disclosure.
Figure 12:
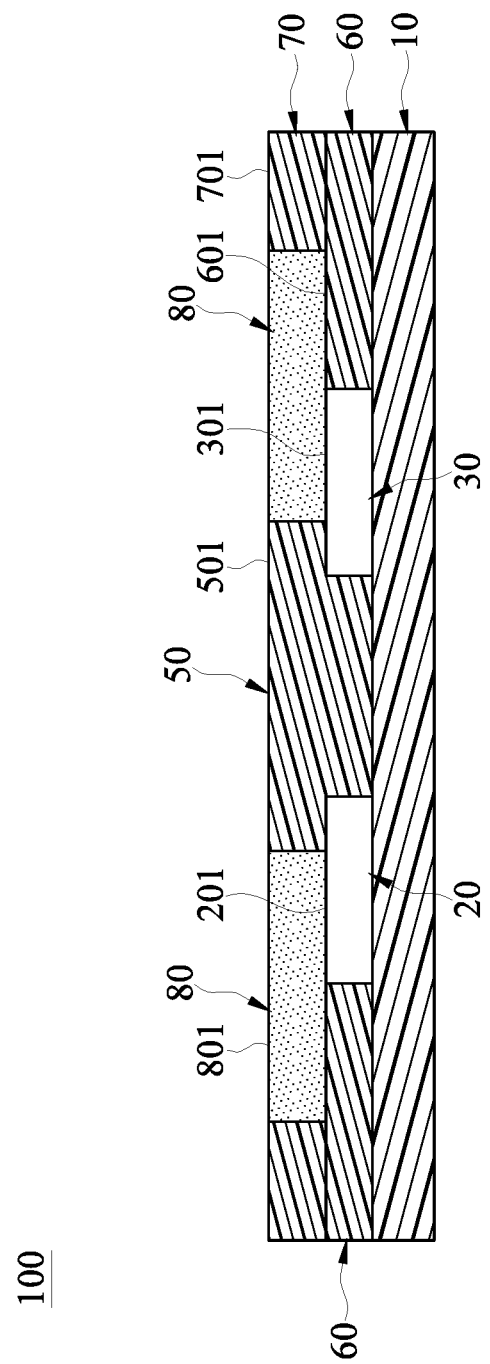
FIG. 12 is a cross-sectional view of the sensing device according to the fourth embodiment of the present disclosure.

Referring to FIG. 10 to FIG. 12, FIG. 10 is a perspective view of a sensing device according to a fourth embodiment of the present disclosure, FIG. 11 is a top view of the sensing device according to the fourth embodiment of the present disclosure, and FIG. 12 is a cross-sectional view of the sensing device according to the fourth embodiment of the present disclosure. The main difference between the present embodiment and the afore-mentioned third embodiment is that the sensing device 100 further includes a ring-shaped blocking structure 70. The ring-shaped blocking structure 70 is formed on the blocking structure 60. The ring-shaped blocking structure 70, the blocking structure 60, and the shielding structure 50 together form two accommodating grooves SP. The encapsulant 80 is correspondingly located in each of the accommodating grooves SP. Specifically, the ring-shaped blocking structure 70 may be a substantially rectangular frame body. As shown in FIG. 7 and FIG. 10, in practical applications, a relevant operator may first circularly remove a portion of the encapsulant 80 and a portion of the shielding structure 50 of the sensing device 100 as shown in FIG. 7, and then form the ring-shaped blocking structure 70 on the encapsulant 80 and the shielding structure 50, so as to form the sensing device 100 as shown in FIG. 10.

The ring-shaped blocking structure 70 and the blocking structure 60 are also used to prevent the sensing light beam emitted by the emitting chip 20 from directly entering the side surface of the receiving chip 30. In practical applications, a penetration rate of the ring-shaped blocking structure 70 for the sensing light beam may be the same as a penetration rate of the blocking structure 60 for the sensing light beam. The ring-shaped blocking structure 70, the blocking structure 60, and the shielding structure 50 may be made of the same material.

In different embodiments, the ring-shaped blocking structure 70 adjacent to the emitting chip 20 may reflect the sensing light beam to improve a utilization of the sensing light beam emitted by the emitting chip 20. The ring-shaped blocking structure 70 adjacent to the receiving chip 30 can absorb the light outside the wavelength band corresponding to the sensing light beam, so that the receiving chip 30 can better receive the sensing light beam. The shape, thickness, height of the ring-shaped blocking structure 70 can be changed according to requirements and is not limited herein.

Each encapsulant 80 is correspondingly located above each chip (the emitting chip 20 and the receiving chip 30). Each encapsulant 80 can absorb the light outside the wavelength band corresponding to the sensing light beam, so that the receiving chip 30 can better receive the sensing light beam. Of course, in different embodiments, the encapsulant 80 may only be used to protect the emitting chip 20 and the receiving chip 30, and the encapsulant 80 may not have the function of absorbing the light outside the wavelength band corresponding to the sensing light beam. In practical applications, the encapsulant 80 may be selectively doped with dyes according to the wavelength of the sensing light beam emitted by the emitting chip 20, so that the dye-doped encapsulant 80 can absorb light in the wavelength band corresponding to the non-sensing light beam. Accordingly, noise of the non-sensing light beam received by the receiving chip 30 can be reduced.

Figure 13:
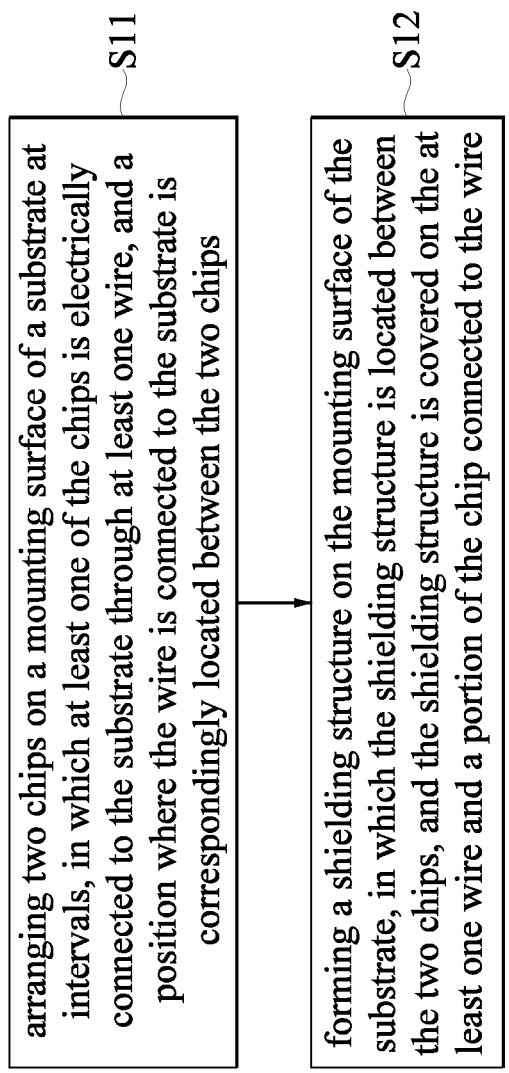
FIG. 13 is a schematic flow chart of a manufacturing method of the sensing device according to the first embodiment of the present disclosure.

In practical applications, a top surface 801 of each encapsulant 80 away from the blocking structure 60, a top surface 701 of the ring-shaped blocking structure 70 away from the blocking structure 60, and a top surface 501 of the shielding structure 50 may be flush with each other, but the present disclosure is not limited thereto. Referring to FIG. 1 and FIG. 13, FIG. 13 is a schematic flow chart of a manufacturing method of the sensing device according to the first embodiment of the present disclosure, and FIG. 1 is a perspective view of the sensing device produced by the manufacturing method of the sensing device according to the first embodiment of the present disclosure. The manufacturing method of the sensing device includes the following steps.

A chip mounting step S11 includes: arranging two chips on a mounting surface 101 of a substrate 10 at intervals. One of the chips is an emitting chip 20, the emitting chip 20 can emit a sensing light beam, another one of the chips is a receiving chip 30, and the receiving chip 30 can receive the sensing light beam. Further, at least one of the chips is electrically connected to the substrate 10 through at least one wire 40, and a position where the wire 40 is connected to the substrate 10 is correspondingly located between the two chips.

A shielding structure forming step S12 includes: forming a shielding structure 50 on the mounting surface 101 of the substrate 10, in which the shielding structure 50 is located between the two chips, and the shielding structure 50 is covered on the wire 40 and a portion of the chip connected to the wire 40. In practical applications, in the shielding structure forming step S12, a mold can be used to form the shielding structure 50 on the mounting surface 101 of the substrate 10.

As shown in FIG. 4, the manufacturing method of the sensing device of the present disclosure is applied to an embodiment in which each chip is connected to the substrate 10 through a wire 40, each wire 40 is located between the two chips, and each wire 40 is covered by the shielding structure 50. In addition, in practical applications, after the shielding structure forming step S12, an encapsulant 80 may be formed on the substrate 10 to cover the two chips according to requirements.

Figure 14:
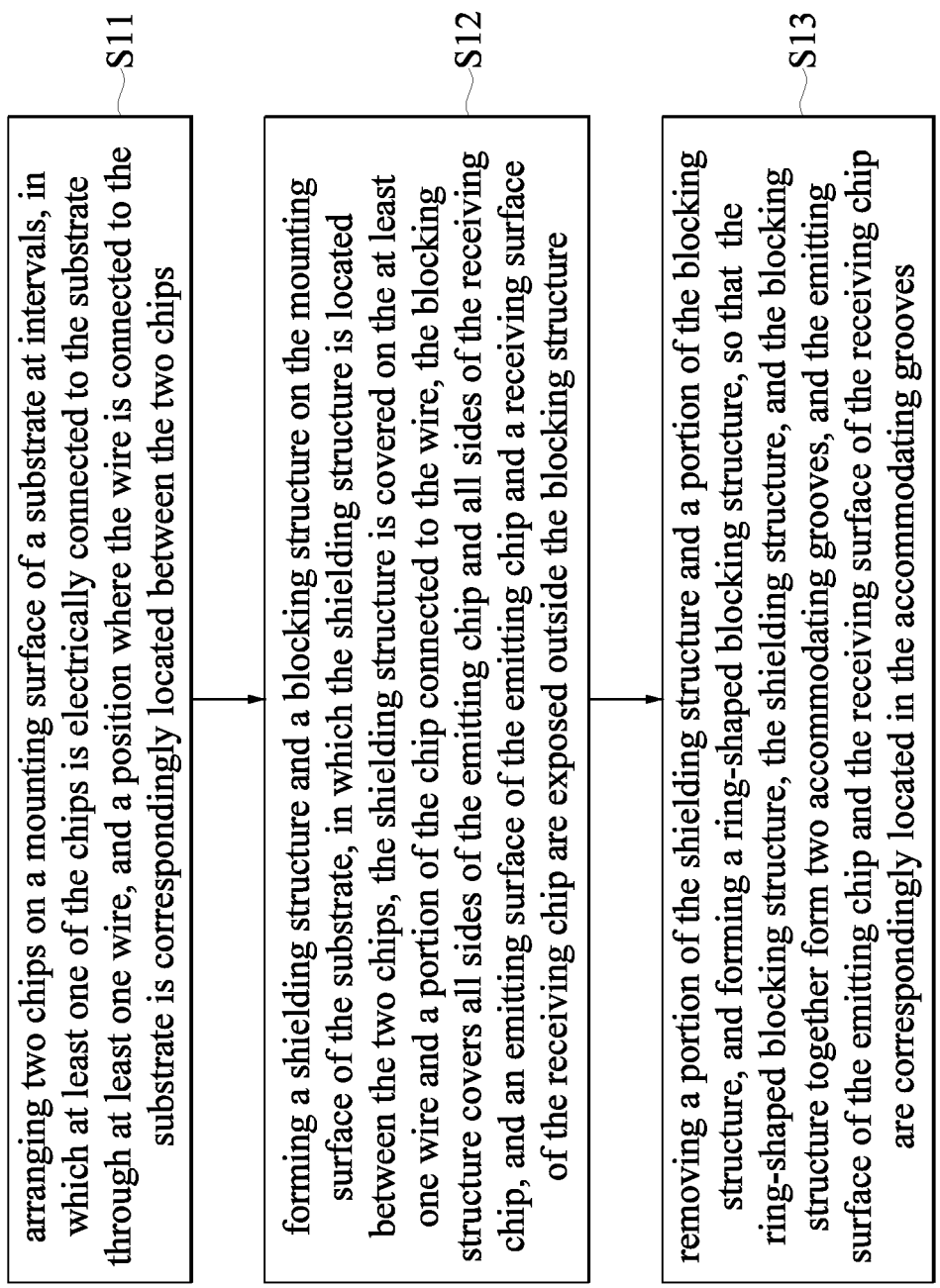
FIG. 14 is a schematic flow chart of a manufacturing method of the sensing device according to the second embodiment of the present disclosure.
Figure 15:
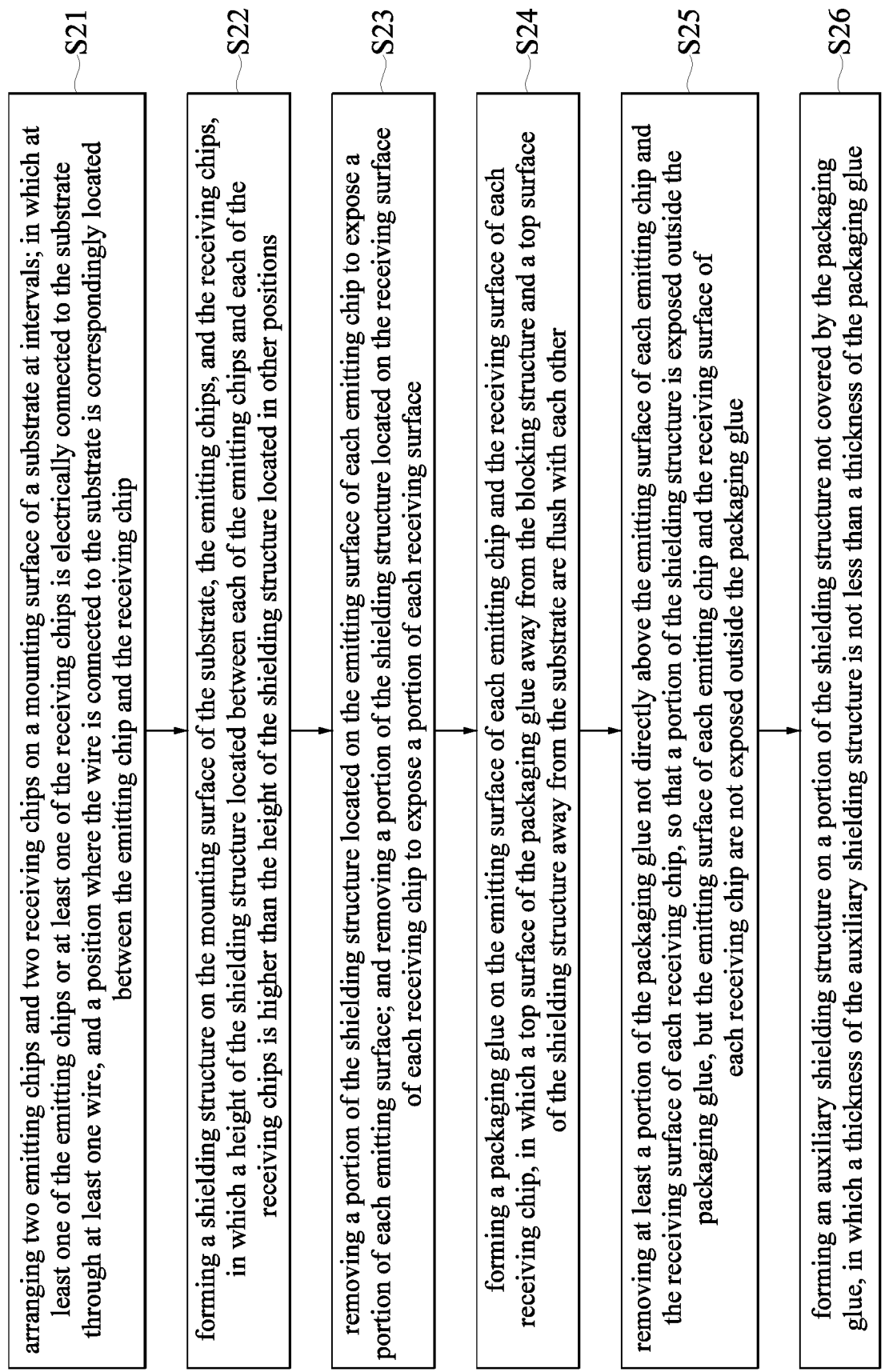
FIG. 15 is a schematic flow chart of a manufacturing method of the sensing device according to the third embodiment of the present disclosure.

Referring to FIG. 14 and FIG. 7, FIG. 14 is a schematic flow chart of a manufacturing method of the sensing device according to the second embodiment of the present disclosure. The main difference between the present embodiment and the afore-mentioned embodiment is that in the shielding structure forming step S12, in addition to forming the shielding structure 50, a blocking structure 60 is also formed at the same time. The blocking structure 60 covers all sides of the emitting chip 20 and all sides of the receiving chip 30. The emitting surface 201 of the emitting chip 20 and the receiving surface 301 of the receiving chip 30 are exposed from the blocking structure 60. The blocking structure 60 has been described in detail in the foregoing description, and will not be reiterated herein.

Another difference between the present embodiment and the foregoing embodiment is that after the shielding structure forming step S12, the manufacturing method of the sensing device further includes a ring-shaped blocking structure forming step S13. The ring-shaped blocking structure forming step S13 includes: removing a portion of the shielding structure 50 and a portion of the blocking structure 60, and forming a ring-shaped blocking structure 70. The ring-shaped blocking structure 70, the shielding structure 50, and the blocking structure 60 together form two accommodating grooves SP. The emitting surface 201 of the emitting chip 20 and the receiving surface 301 of the receiving chip 30 are correspondingly located in the accommodating grooves SP. The detailed descriptions of the ring-shaped blocking structure 70 and the encapsulant 80 are described in the foregoing description, and will not be repeated herein.

Figure 27:
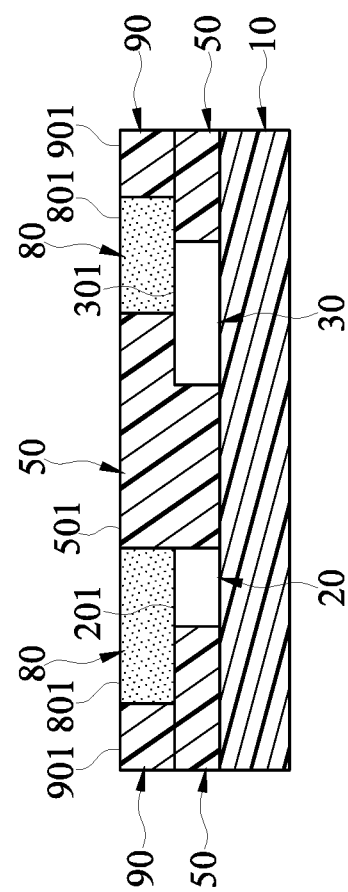
FIG. 26 and FIG. 27 are respectively a top view and a cross-sectional view of a sensing device produced by the manufacturing method of the sensing device according to the third embodiment of the present disclosure.

Referring to FIG. 15 to FIG. 28, FIG. 15 is a schematic flow chart of a manufacturing method of the sensing device according to the third embodiment of the present disclosure. FIG. 16 to FIG. 25 are respectively schematic diagrams showing semi-finished products of the sensing device in the manufacturing processes of the manufacturing method of the sensing device according to the third embodiment of the present disclosure. FIG. 26 and FIG. 27 are respectively a top view and a cross-sectional view of a sensing device produced by the manufacturing method of the sensing device according to the third embodiment of the present disclosure. The manufacturing method of the sensing device of the present embodiment includes the following steps.

Figure 17:
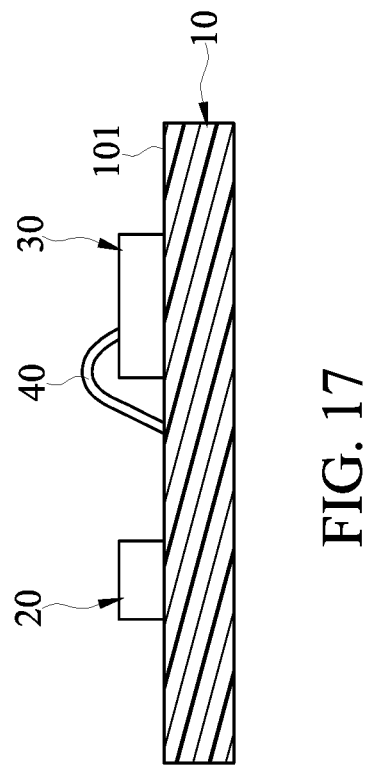
FIG. 16 to FIG. 25 are respectively schematic diagrams showing semi-finished products of the sensing device in the manufacturing processes of the manufacturing method of the sensing device according to the third embodiment of the present disclosure.
Figure 16:
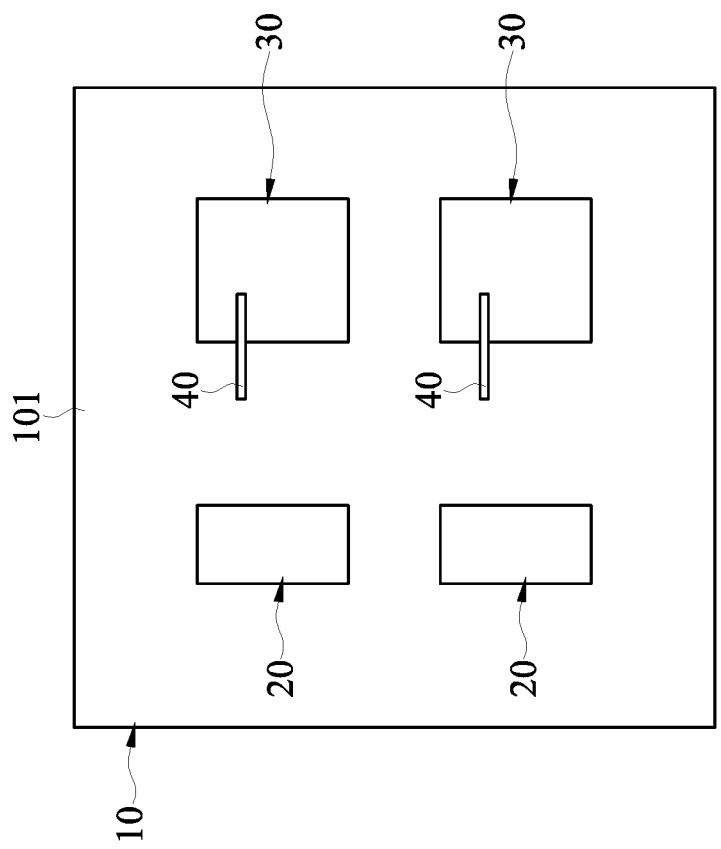

A chip mounting step S21 includes: arranging two emitting chips 20 and two receiving chips 30 on a mounting surface 101 of a substrate 10 at intervals as shown in FIG. 16 and FIG. 17. That is, two of the chips are the emitting chips 20 that can respectively emit a sensing light beam, and the other two of the chips are the receiving chips 30 that can respectively receive the sensing light beam. Further, at least one of the chips is electrically connected to the substrate 10 through at least one wire 40, and a position where the wire 40 is connected to the substrate 10 is correspondingly located between the emitting chip 20 and the receiving chip 30.

Figure 19:
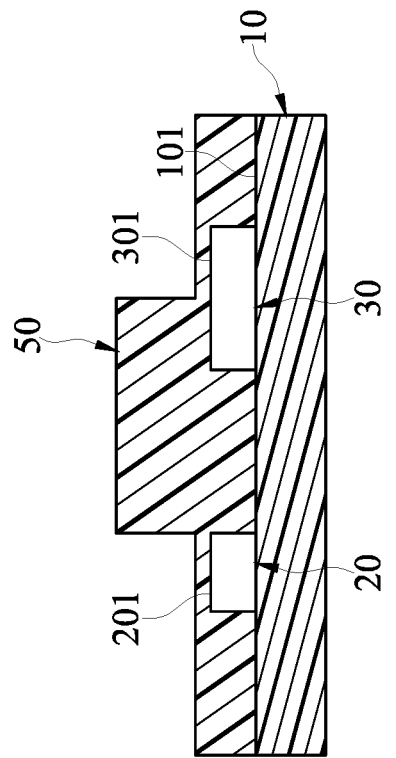
Figure 18:
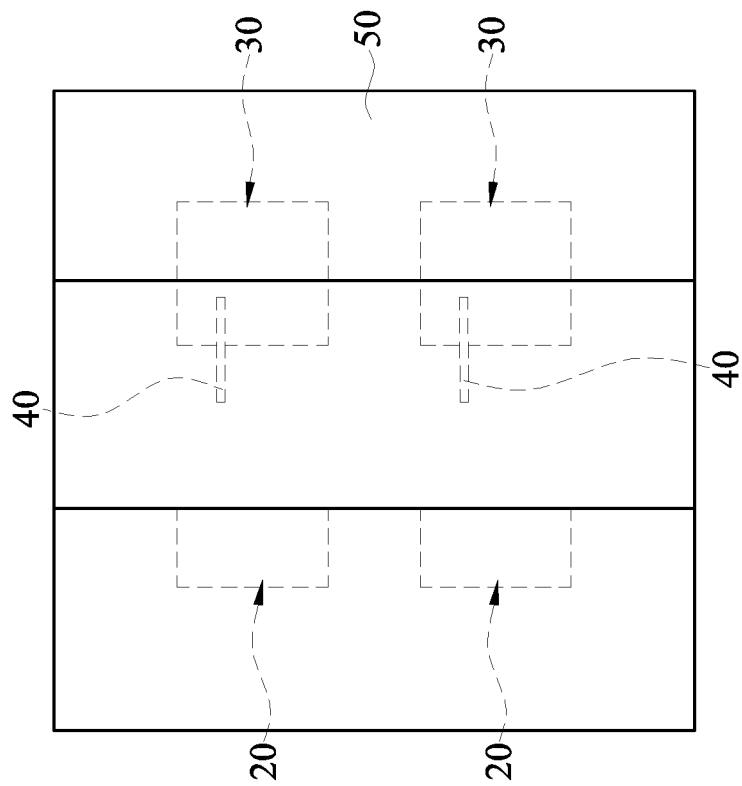

A shielding structure forming step S22 includes: forming a shielding structure 50 on the mounting surface 101 of the substrate 10, each of the emitting chips 20, and each of the receiving chips 30. In addition, a height of the shielding structure 50 located between each of the emitting chips 20 and each of the receiving chips 30 is greater than the height of the shielding structure 50 located in other positions as shown in FIG. 18 and FIG. 19. The shielding structure 50 completely covers each of the wires 40 and a portion where each of the chips is connected to the wire 40.

Figure 21:
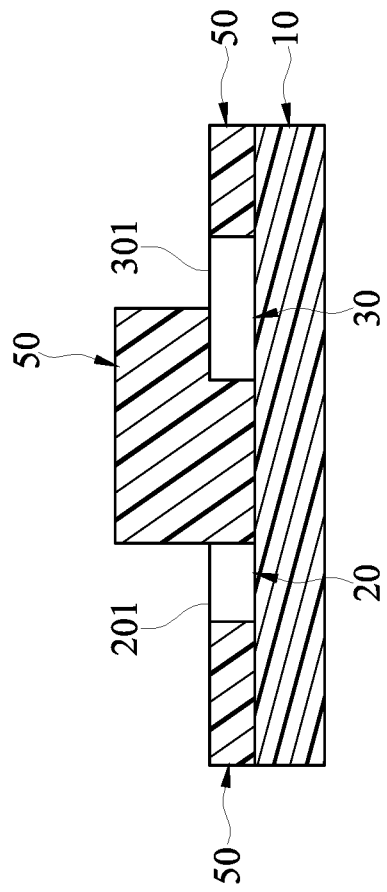
Figure 20:
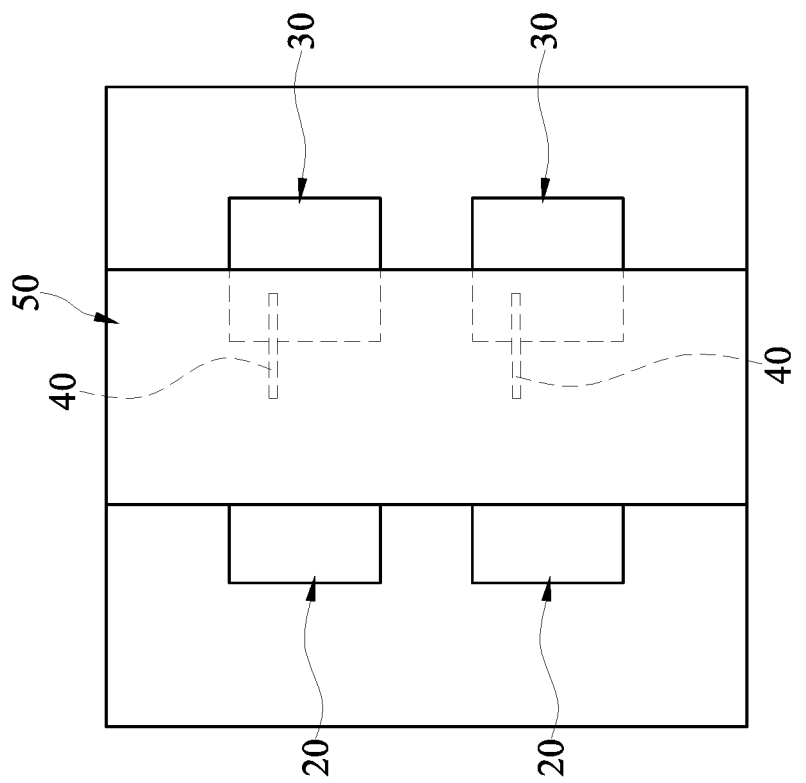

A surface exposing step S23 includes: removing a portion of the shielding structure 50 located on the emitting surface 201 of each emitting chip 20 to expose a portion of each emitting surface 201; and removing a portion of the shielding structure 50 located on the receiving surface 301 of each receiving chip 30 to expose a portion of each receiving surface 301 as shown in FIG. 20 and FIG. 21.

Figure 23:
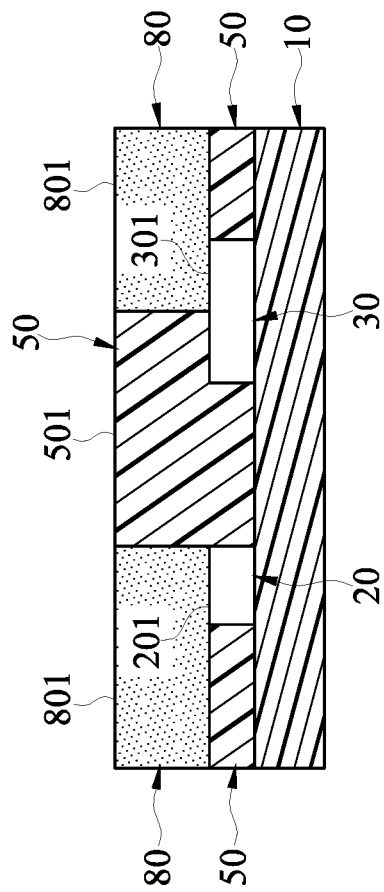
Figure 22:
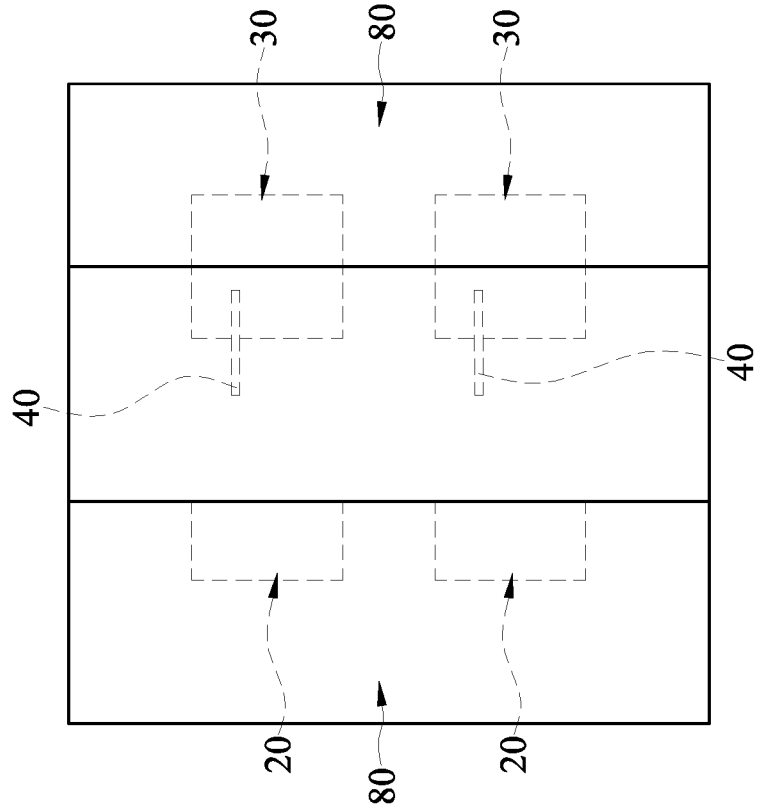

An encapsulant forming step S24 includes: forming an encapsulant 80 on the emitting surface 201 of each emitting chip 20 exposed outside the shielding structure 50 and the receiving surface 301 of each receiving chip 30 exposed outside the shielding structure 50. Further, a top surface 801 of the encapsulant 80 away from the blocking structure 60 and a top surface 501 of the shielding structure 50 away from the substrate 10 are flush with each other as shown in FIG. 22 and FIG. 23.

Figure 25:
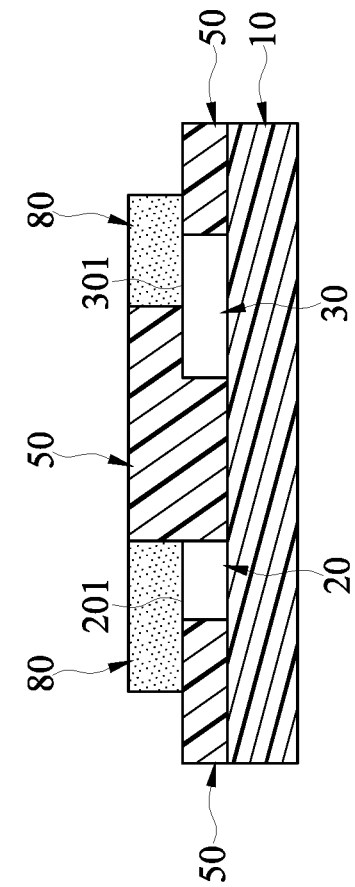
Figure 24:
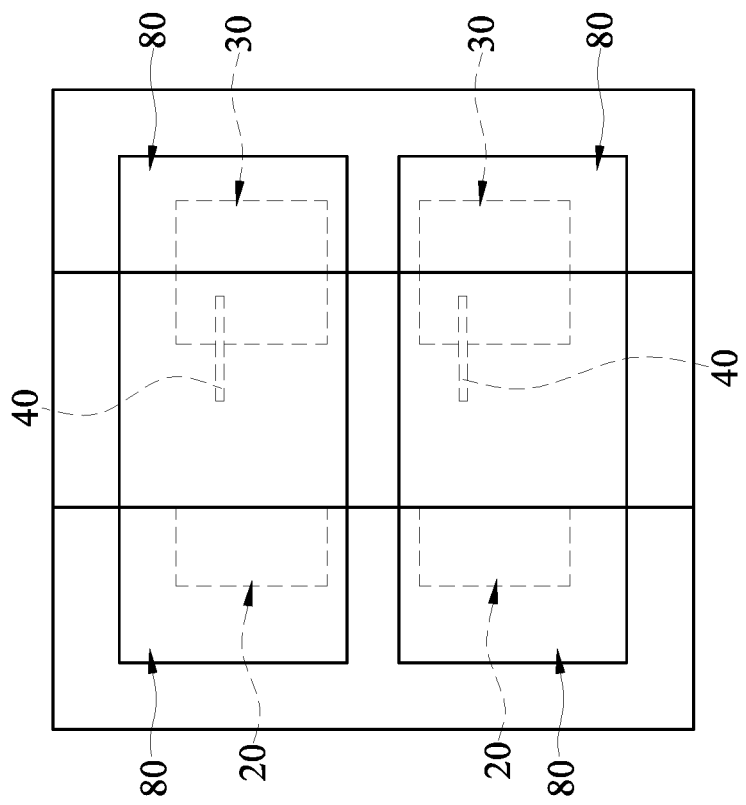
Figure 26:
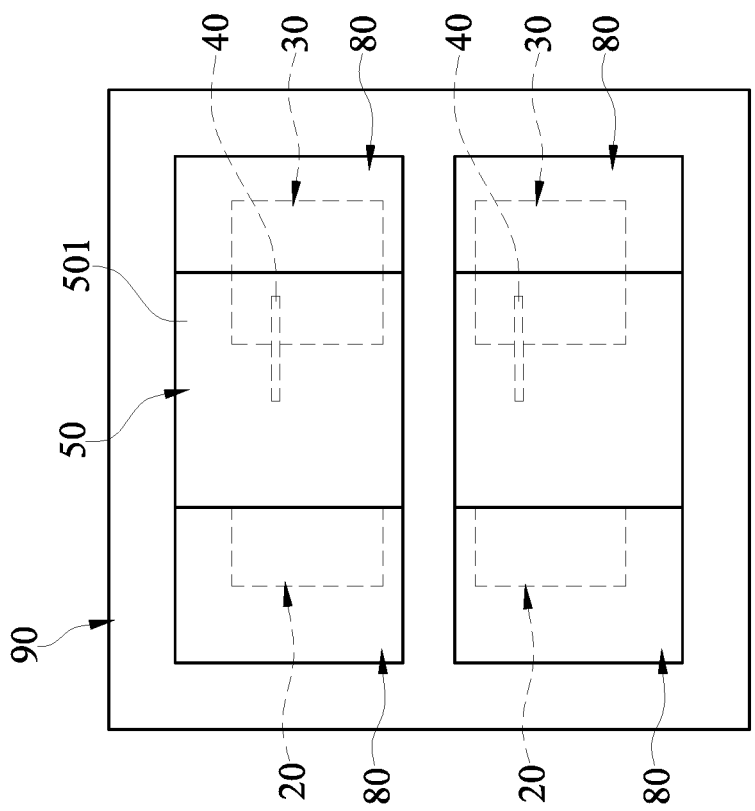

A cutting step S25 includes: removing at least a portion of the encapsulant 80 not directly above the emitting surface 201 of each emitting chip 20 and the receiving surface 301 of each receiving chip 30, so that a portion of the shielding structure 50 is exposed outside the encapsulant 80, but the emitting surface 201 of each emitting chip 20 and the receiving surface 301 of each receiving chip 30 are not exposed outside the encapsulant 80 as shown in FIG. 24 and FIG. 25.

An auxiliary shielding structure forming step S26 includes: forming an auxiliary shielding structure 90 on a portion of the shielding structure 50 not covered by the encapsulant 80, in which a thickness of the auxiliary shielding structure 90 is equal to a thickness of the encapsulant 80 as shown in FIG. 26 and FIG. 27. In practical applications, the thickness of the auxiliary shielding structure 90 may be between 0.2 mm and 0.3 mm, and the auxiliary shielding structure 90 referred to herein is the same as the aforementioned ring-shaped blocking structure 70. Relevant descriptions are as described above. The auxiliary shielding structure 90 and the ring-shaped blocking structure 70 may be made of the same material.

As described above, as shown in FIG. 26 and FIG. 27, the sensing device produced by the manufacturing method according to the third embodiment of the present disclosure is illustrated. In the present embodiment, one of the emitting chips 20 is configured to emit a red light beam, and another one of the emitting chips 20 is configured to emit a green light beam. Correspondingly, one of the receiving chips 30 is configured to receive the red light beam, and another one of the receiving chips 30 is configured to receive the green light beam.

It should be noted that, as shown in FIG. 24, in practical applications, in the cutting step S25, in addition to removing the encapsulant 80 in a ring shape, portions of the encapsulant 80 and the shielding structure 50 between the two emitting chips 20 can be removed, and portions of the encapsulant 80 and the shielding structure 50 between the two receiving chips 30 can also be removed. That is, the portions of the shielding structure 50 and the encapsulant 80 can be removed in an H-shaped manner.

In practical applications, in the above-mentioned shielding structure forming step S22, a height H1 of the shielding structure 50 is greater than a height of each of the chips (the emitting chip 20 and the receiving chip 30). In a preferred application, the height H1 of the shielding structure 50 is greater than a sum of a height of the emitting chip 20 and a width of the emitting chip 20, divided by 2*tan θ, in which θ is a half-value angle of the emitting chip 20. In addition, a difference between the height of the shielding structure 50 and the height of each of the chips (the emitting chip 20 and the receiving chip 30) is not greater than 50 micrometers (um), and the width of the shielding structure 50 is between 0.5 millimeter (mm) and 0.85 millimeter (mm).

Figure 28:
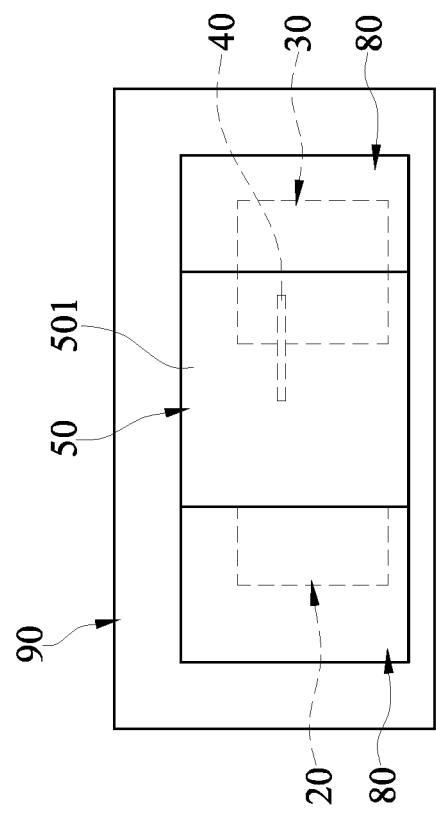
FIG. 28 is a schematic diagram of the sensing device produced by the manufacturing method of the sensing device according to the third embodiment of the present disclosure.

As shown in FIG. 28, a top view of the sensing device produced by the manufacturing method according to the fourth embodiment of the present disclosure is illustrated. After the auxiliary shielding structure forming step S26 of the manufacturing method of the third embodiment, the manufacturing method of the fourth embodiment further includes: cutting the sensing device shown in FIG. 26 and FIG. 27, so that the two emitting chips 20 are separated from each other, and the two receiving chips 30 are separated from each other. Accordingly, the sensing device shown in FIG. 26 can be cut into a state shown in FIG. 28.

It should be noted that the sensing device 100 mentioned in the foregoing embodiments can be manufactured using the manufacturing method of the sensing device 100 mentioned in the present embodiment, but the present disclosure is not limited thereto.

In conclusion, the manufacturing method of the sensing device of the present disclosure is to first arrange chips on the substrate, and then form a shielding structure between the emitting chip and the receiving chip. The shielding structure covers the wire between the emitting chip and the receiving chip. Therefore, a size of the sensing device produced by the manufacturing method of the sensing device of the present disclosure can be smaller than a size of the sensing device produced by a conventional manufacturing method.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A sensing device, comprising:
   a substrate;
   two chips, which are respectively defined as an emitting chip and a receiving chip;
   wherein the emitting chip is capable of emitting a sensing light beam, the receiving chip is capable of receiving the sensing light beam, and the two chips are fixed in position on the substrate at intervals; wherein the chips are electrically connected to the substrate through two wires, and a position where each of the wires is connected to the substrate is located between the two chips; and a shielding structure formed on the substrate; wherein the shielding structure is located between the two chips, and the shielding structure covers the wires and two portions of the chips connected to the wires;

wherein, in a top view of the sensing device, a sum of a distance from a position where each of the wires is connected to the substrate to a position where each of the wires is connected to the chip is greater than a width of the shielding structure.

2. The sensing device according to claim 1, further comprising: an encapsulant, the encapsulant covering each of the chips.

3. The sensing device according to claim 2, wherein the encapsulant is configured to absorb light outside of a wavelength band corresponding to the sensing light beam.

* * * * *